US010736516B2

(12) United States Patent
Sharma

(10) Patent No.: US 10,736,516 B2
(45) Date of Patent: Aug. 11, 2020

(54) METHOD AND APPARATUS FOR ACCURATELY DETERMINING HEART RATE VARIABILITY AND SYMPATHETIC RESERVE

(71) Applicant: Medtronic, Inc., Minneapolis, MN (US)

(72) Inventor: Vinod Sharma, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 797 days.

(21) Appl. No.: 14/172,378

(22) Filed: Feb. 4, 2014

(65) Prior Publication Data

US 2015/0141851 A1 May 21, 2015

Related U.S. Application Data

(60) Provisional application No. 61/907,056, filed on Nov. 21, 2013.

(51) Int. Cl.
*A61B 5/024* (2006.01)
*A61B 5/0205* (2006.01)
(Continued)

(52) U.S. Cl.
CPC ........ *A61B 5/0205* (2013.01); *A61B 5/02405* (2013.01); *A61B 5/0408* (2013.01);
(Continued)

(58) Field of Classification Search
CPC . A61B 5/0205; A61B 5/0432; A61B 5/04012; A61B 5/1118; A61B 5/0408;
(Continued)

(56) References Cited

U.S. PATENT DOCUMENTS 4,223,678 A 9/1980 Langer et al.
4,374,382 A 2/1983 Markowitz
(Continued)

OTHER PUBLICATIONS

Wang (Translation Only, Buqing et al., "Research Progress of the Methods for Heart Rate Variability Analysis" Beijing Biomedical Engineering vol. 26 (Year: 2007).*

(Continued)

*Primary Examiner* — Puya Agahi

(57) ABSTRACT

An implantable monitoring device is disclosed for monitoring a patient's heart rate variability over time. The device includes a cardiac electrogram amplifier, a sensing electrode coupled to an input of the amplifier, timing circuitry, processing circuitry and a memory. The timing circuitry defines successive shorter time periods during each monitoring period. The processing circuitry relies upon electrogram activity that occurs during rest periods that extend as long as T1, all of which is stored into memory. Active periods are not considered as part of the heart rate variability calculation. The processing circuitry calculates median intervals between depolarizations of the patient's heart sensed by the amplifier during the shorter time periods and calculates a standard deviation of the median intervals during T2, a longer monitoring period.

22 Claims, 14 Drawing Sheets

(51) Int. Cl.
*A61B 5/11* (2006.01)
*A61B 5/04* (2006.01)
*A61B 5/00* (2006.01)
*A61B 5/0464* (2006.01)
*A61B 5/0408* (2006.01)
*A61B 5/0432* (2006.01)

(52) U.S. Cl.
CPC ........ *A61B 5/04012* (2013.01); *A61B 5/0432* (2013.01); *A61B 5/0464* (2013.01); *A61B 5/1118* (2013.01); *A61B 5/686* (2013.01)

(58) Field of Classification Search
CPC .... A61B 5/0464; A61B 5/02405; A61B 5/686
See application file for complete search history.

(56) References Cited

U.S. PATENT DOCUMENTS

| | | | |
|---|---|---|---|
| 4,428,378 A | 1/1984 | Anderson et al. | |
| 4,972,842 A | 11/1990 | Korten et al. | |
| 5,088,488 A | 2/1992 | Markowitz et al. | |
| 5,107,833 A | 4/1992 | Barsness | |
| 5,117,824 A | 6/1992 | Keimel et al. | |
| 5,135,004 A | 8/1992 | Adams et al. | |
| 5,168,871 A | 12/1992 | Grevious | |
| 5,292,343 A | 3/1994 | Blanchette et al. | |
| 5,312,446 A | 5/1994 | Holschbach et al. | |
| 5,314,450 A | 5/1994 | Thompson | |
| 5,324,315 A | 6/1994 | Grevious | |
| 5,330,513 A | 7/1994 | Nichols et al. | |
| 5,331,966 A | 7/1994 | Bennett et al. | |
| 5,354,319 A | 10/1994 | Wyborny et al. | |
| 5,383,909 A | 1/1995 | Keimel | |
| 5,411,031 A | 5/1995 | Yomtov | |
| 5,431,689 A | 7/1995 | Weinberg et al. | |
| 5,437,285 A | 8/1995 | Verrier et al. | |
| 5,466,245 A * | 11/1995 | Spinelli | A61N 1/3627 607/17 |
| 5,497,780 A | 3/1996 | Zehender | |
| 5,513,645 A | 5/1996 | Jacobson et al. | |
| 5,545,186 A | 8/1996 | Olson et al. | |
| 5,603,331 A | 2/1997 | Heemels et al. | |
| 5,682,901 A | 11/1997 | Kamen | |
| 5,722,999 A | 3/1998 | Snell | |
| 5,749,900 A | 5/1998 | Schroeppel et al. | |
| 5,755,736 A | 5/1998 | Gillberg et al. | |
| 5,957,855 A | 9/1999 | Oriol et al. | |
| 5,967,995 A | 10/1999 | Shusterman et al. | |
| 6,026,320 A | 2/2000 | Carlson et al. | |
| 6,035,233 A | 3/2000 | Schroeppel et al. | |
| 6,144,878 A | 7/2000 | Prutchi et al. | |
| 6,480,733 B1 * | 11/2002 | Turcott | A61B 5/0002 600/509 |
| 6,508,771 B1 * | 1/2003 | Padmanabhan | A61N 1/3702 600/515 |
| 6,752,765 B1 * | 6/2004 | Jensen | A61N 1/36521 600/536 |
| 7,572,226 B2 | 8/2009 | Carlson et al. | |
| 7,833,764 B2 | 11/2010 | Carlson et al. | |
| 7,937,149 B2 | 5/2011 | Stadler et al. | |
| 7,970,467 B2 | 6/2011 | Carlson et al. | |
| 8,131,373 B2 | 3/2012 | Libbus | |
| 8,280,510 B2 | 10/2012 | Dyjach et al. | |

OTHER PUBLICATIONS (PCT/US2014/066825) PCT Notification of Transmittal of the International Search Report and the Written Opinion of the International Searching Authority.

Wang, Buqing et al., "Research Progress of the Methods for Heart Rate Variability Analysis" Beijing Biomedical Engineering vol. 26, No. 5 pp. 551-554.

* cited by examiner

| Time of day | Time segment # | Active (A)/Inactive (I) | Median R-R (ms) |
|---|---|---|---|
| 12:05:00AM | 1 | I | 1000 |
| 12:10:00AM | 2 | I | 960 |
| 12:15:00AM | 3 | I | 990 |
| 12:20:00AM | 4 | I | 950 |
| 6:00:00AM | 5 | I | 1100 |
| 12:30:30AM | 6 | I | 930 |
| 12:35:00AM | 7 | I | 960 |
| 12:40:00AM | 8 | I | 920 |
| 12:45:00AM | 9 | I | 1000 |
| 12:50:00AM | 10 | I | 1200 |
| 12:55:00AM | 11 | I | 1300 |
| 1:00:00AM | 12 | I | 950 |

1 AM - 2 AM ⋮

2 AM - 3 AM ⋮

3 AM - 4 AM ⋮

4 AM - 5 AM ⋮

5 AM - 6 AM ⋮

6 AM - 7 AM ⋮

7 AM - 8 AM ⋮

8 AM - 9 AM

| Time of day | Time segment # | Active (A)/Inactive (I) | Median R-R (ms) |
|---|---|---|---|
| 8:05:00AM | 97 | A | ~~900~~ |
| 8:10:00AM | 98 | A | ~~800~~ |
| 8:15:00AM | 99 | A | ~~810~~ |
| 8:20:00AM | 100 | I | 940 |
| 8:25:00AM | 101 | I | 1000 |
| 8:30:30AM | 102 | A | ~~900~~ |
| 8:35:00AM | 103 | A | ~~860~~ |
| 8:40:00AM | 104 | I | 960 |
| 8:45:00AM | 105 | I | 1000 |
| 8:50:00AM | 106 | I | 1100 |
| 8:55:00AM | 107 | I | 990 |
| 9:00:00AM | 108 | A | ~~900~~ |

9 AM - 10 AM ⋮

10 AM - 11 AM ⋮

11 AM - 12 Noon ⋮

⋮

11 PM - 12 AM ⋮

HRV = 60 ms
[Standard Deviation of all median R-R intervals during inactive (I) periods]

FIG. 14

METHOD AND APPARATUS FOR ACCURATELY DETERMINING HEART RATE VARIABILITY AND SYMPATHETIC RESERVE

RELATED APPLICATION

The present application claims priority and other benefits from U.S. Provisional Patent Application Ser. No. 61/907,056, filed Nov. 21, 2013, entitled "METHOD AND APPARATUS FOR ACCURATELY DETERMINING HEART RATE VARIABILITY AND SYMPATHETIC RESERVE", incorporated herein by reference in its entirety.

BACKGROUND

The present disclosure relates generally to implantable medical devices, and, more particularly, to implantable medical devices intended for use in monitoring a patient's heart rhythm.

Implantable pacemakers and cardioverters monitor the heart's rhythm in order to detect arrhythmias and deliver appropriate therapies to terminate detected arrhythmias. In conjunction with this function, the ability of the device is to store information with regard to monitored heart rhythms has dramatically increased over the past two years. Examples of implantable pacemakers and defibrillators which have the capability of storing information related to monitor heart rhythms include U.S. Pat. No. 4,223,678 issued to Langer et al., U.S. Pat. No. 5,722,999 issued to Snell, U.S. Pat. No. 5,513,645 issued to Jacobsen et al. and U.S. Pat. No. 5,312,446 issued to Holschbach et al. In addition, there are subcutaneously implantable monitoring devices which do not deliver any anti-arrhythmia therapies to the heart but simply store information regarding a patient's heart rhythms for later uplink to an external device. Such devices are disclosed in U.S. Pat. No. 5,331,966 issued to Bennett et al., U.S. Pat. No. 5,135,004 issued to Adams and U.S. Pat. No. 5,497,780 issued to Zehender.

Data stored relating to a patient's heart rhythm may include information relating to heart rate trends over time, as disclosed in U.S. Pat. No. 5,088,488 issued to Markowitz et al., U.S. Pat. No. 5,330,513 issued to Nichols et al. and U.S. Pat. No. 5,603,331 issued to Heemels et al., as well as information relating to heart rate variability over time, as disclosed in U.S. Pat. No. 5,749,900 issued to Schroeppel et. al., U.S. Pat. No. 5,466,245 issued to Spinelli et al., U.S. Pat. No. 5,411,131 issued to Yomtov et al. and U.S. Pat. No. 5,437,285 issued to Verrier et al.

Typically, measurements of heart rate variability in such devices is accomplished by employing one of the standard measurements of heart rate variability such as the standard deviation of all normal-to-normal (SDNN) or standard deviation of average normal-to-normal (SDANN) indices, described in U.S. Pat. No. 5,749,900 issued to Schroeppel et al. and U.S. Pat. No. 5,411,031 issued to Yomtov, cited above. Another method to measure heart rate variability is described in U.S. Pat. No. 6,508,771 issued to Padmanabhan et al. in which median atrial interval value is measured every five minutes and then the standard deviation of these intervals is computed over a certain period of time.

Heart rate variability can be useful for determining cardiac sympathetic reserve, which can be helpful in determining whether a patient may benefit from cardiac therapies (e.g. cardiac resynchronization therapy (CRT)). Patients responsive to CRT typically exhibit a baseline sympathetic uptake function that indicates a preserved sympathetic function. In contrast, patients that exhibit severely impaired baseline sympathetic function are less likely to benefit from CRT. Present methods that calculate heart rate variability can be less accurate resulting in some patients not receiving implantable medical devices when in fact the patient could benefit from a cardiac therapy. For example, conventional devices determine heart rate variability by measuring a median atrial interval value every five minutes and then computing the standard deviation of these intervals over a 24 hour period. The conventional method can occasionally incorrectly determine that a patient's heart rate variability is decreasing during a period of activity. It is therefore desirable to develop a more accurate method to determine heart rate variability in order to estimate cardiac sympathetic reserve, which, in turn, whether a patient can benefit from cardiac therapy delivered through an implantable medical device.

SUMMARY

The present disclosure more accurately determines heart rate variability by employing accurate assessments of basal autonomic tone. Reliance on basal autonomic tone provides greater precision of diagnostic abnormalities in autonomic tone.

The present disclosure is directed toward an implanted device having enhanced capabilities for monitoring a patient's heart rate variability over extended periods of time. The data collected by the implantable device is stored and can be telemetered to an associated external device such as a device programmer for display and analysis. The collected information and calculated heart rate variability may also be employed to trigger an alarm or alert to the patient and/or physician, in response to a measured calculation of heart rate variability or change in heart rate variability. Heart rates are measured by measuring the time intervals between sensed depolarizations of a chamber of the patient's heart and preceding sensed depolarizations or delivered pacing pulses. Periods of activity during which heart rate and autonomic tone is elevated are associated with declining heart rate variability. When such periods are included in the measurement of daily heart rate variability, the overall heart rate variability is underestimated. This disclosure presents one or more methods in which the effect of such active periods is removed, thus providing a more accurate measure of heart rate variability with potentially greater diagnostic utility.

In addition, particularly valuable in the context of an implanted device, the process for calculation of a median interval is substantially simplified as opposed to the process for calculating the mean values of the measured intervals with ectopic beats and associated measured intervals excluded. Additionally, exclusion of active periods provides a much more accurate measure of heart rate variability.

BRIEF DESCRIPTION OF THE DRAWINGS

FIG. 14 is an exemplary view of active and inactive interval data summarized over a twenty four hour period of time.

DETAILED DESCRIPTION

Figure 1:
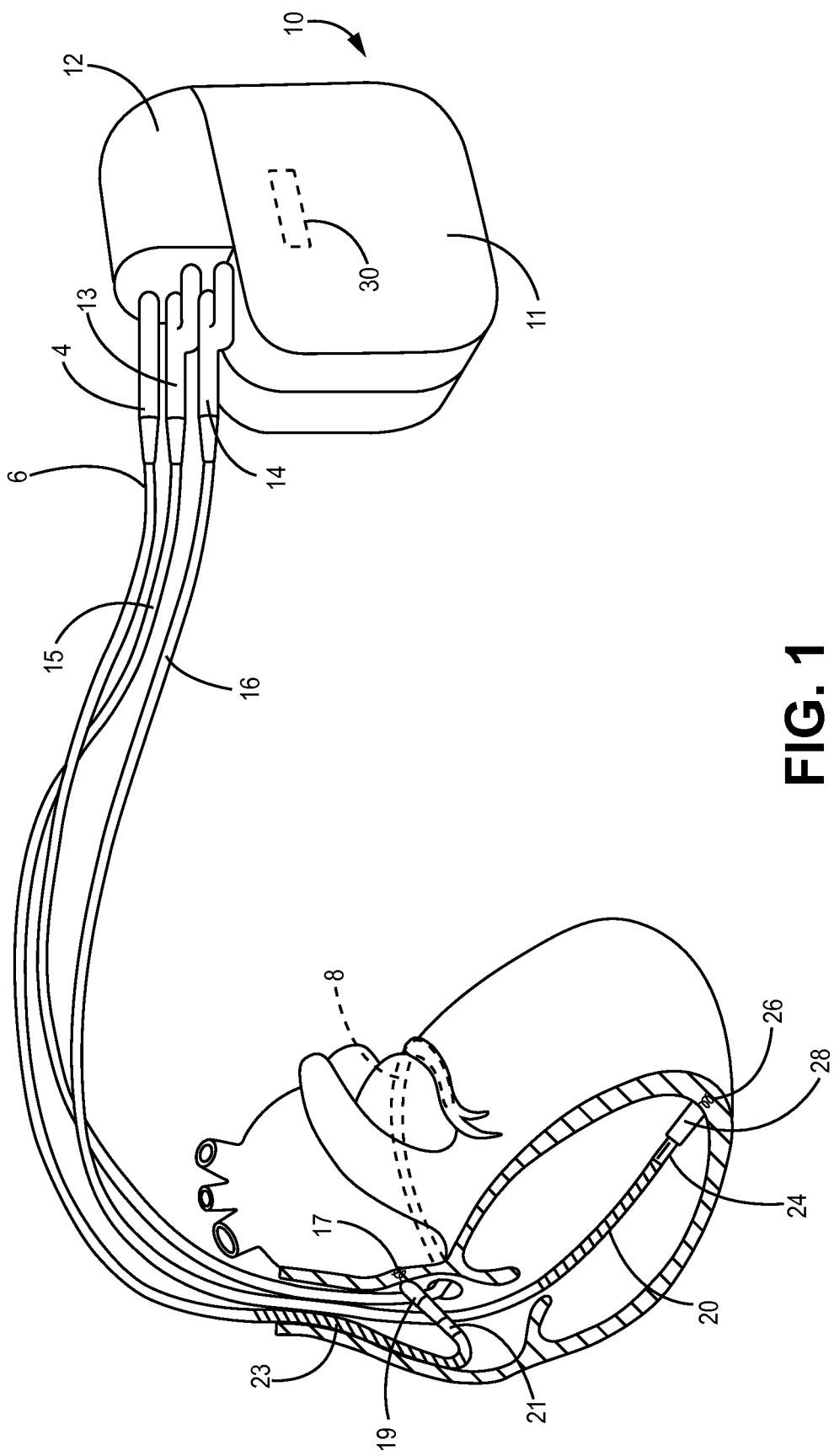
FIG. 1 illustrates an implantable pacemaker/cardioverter/defibrillator of a type useful in practicing the present disclosure, in conjunction with a human heart.

FIG. 1 illustrates a defibrillator and lead set of a type in which the present disclosure may usefully be practiced. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors.

The atrial/SVC lead includes an elongated insulative lead body 15, also carrying three mutually insulated conductors. The atrial/SVC lead is used in acquiring A-A measurements for HRV measurements; however, it should be noted that V-V measurements can also be used for HRV measurements. A-A measurements are preferred since A-A measurements remove the confounding effect of AV node delays. AV node delay can be influenced by disease of conduction system.

Located adjacent to the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13 which carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor.

The implantable medical device (IMD) (e.g. pacemaker/cardioverter/defibrillator etc.) 10 includes a hermetic enclosure 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12 which serves as a receptacle and electrical connector for receiving the connectors 4, 13 and 14 and interconnecting the leads to the circuitry within enclosure 11. An activity sensor 30 is illustrated schematically by broken outline, and may be an accelerometer or a piezoelectric transducer. Sensor 30 may be used for regulation of pacing rate based upon demand for cardiac output.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 2:
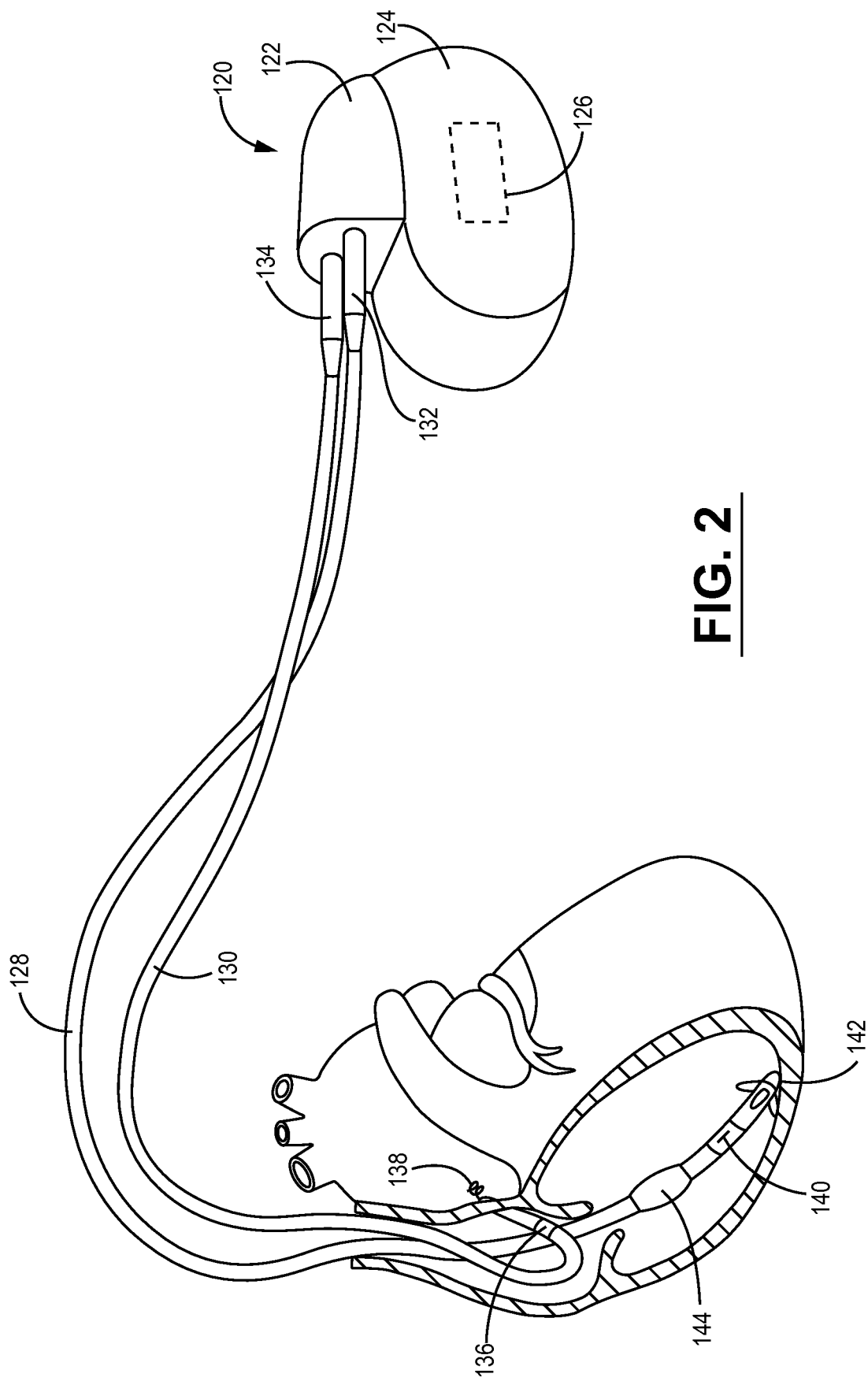
FIG. 2 illustrates an implantable pacemaker of a type useful in practicing the present disclosure, in conjunction with a human heart.

FIG. 2 illustrates a cardiac pacemaker of a type appropriate for use in practicing the present disclosure in conjunction with its associated lead system, illustrated in relation to a patient's heart. The pacemaker 120 includes a hermetic enclosure 124 containing the electronic circuitry used for generating cardiac pacing pulses and for monitoring the patient's heart rhythm. An activity sensor 126 is illustrated schematically by dashed lines, and may be an accelerometer or a piezoelectric transducer as discussed above in conjunction with FIG. 1. Mounted to the enclosure 124 is a header 122 which serves as a receptacle and electrical connector for receiving the connectors 132 and 134 of pacing leads 128 and 130 and interconnecting the leads to the circuitry within enclosure 124. Lead 128 is a ventricular lead provided with electrodes 140 and 142 for monitoring right ventricular heart signals. Also illustrated on lead 128 is a physiologic sensor 144 which may optionally be included in addition to or as an alternative to the activity sensor 126, and which may take the form of an oxygen sensor, pressure sensor, temperature sensor, other sensor of any of the various types employed for monitoring demand for cardiac output or for measuring heart hemodynamics. Sensor 124 may be used in conjunction with or as an alternative to the activity sensor 126 for rate responsive pacing. Atrial lead 130 carries electrodes 136 and 138 and is employed for sensing and pacing the patient's atrium.

Figure 3:
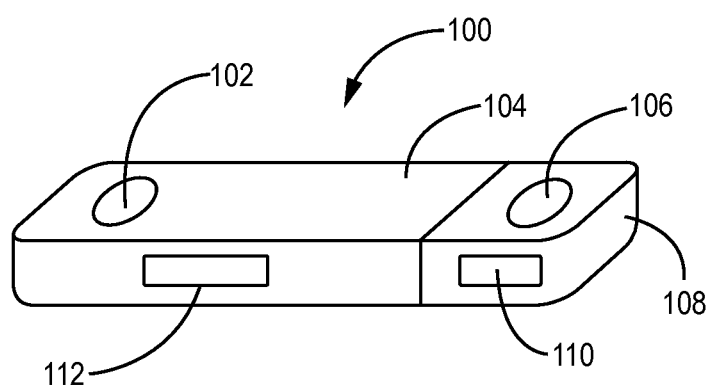
FIG. 3 illustrates an implantable monitor of a type useful in practicing the present disclosure.

FIG. 3 illustrates a subcutaneously implantable monitor of a type appropriate for use in practicing the present disclosure. The monitor shares the external configuration of the Medtronic REVEAL® implantable monitor, and is provided with a hermetically sealed enclosure 104 containing the electronic circuitry used for generating cardiac pacing pulses and for monitoring the patient's heart rhythm and which carries a molded plastic header 108. The enclosure 104 and the header 108 each carry an electrode 102 and 106, respectively for monitoring heart rhythm. Also mounted in the header 108 is an antenna 110 for use in communicating between the device and an external programmer. Illustrated in broken or dashed lines at 112 is an internal activity sensor, of the type typically employed in the context of rate responsive cardiac pacemakers, taking the form either of an accelerometer or a piezo-electric transducer. Heart signals are detected between the electrodes 102 and 106 and measurements of physical activity are detected by sensor 112 for storage and analysis.

Figure 4:
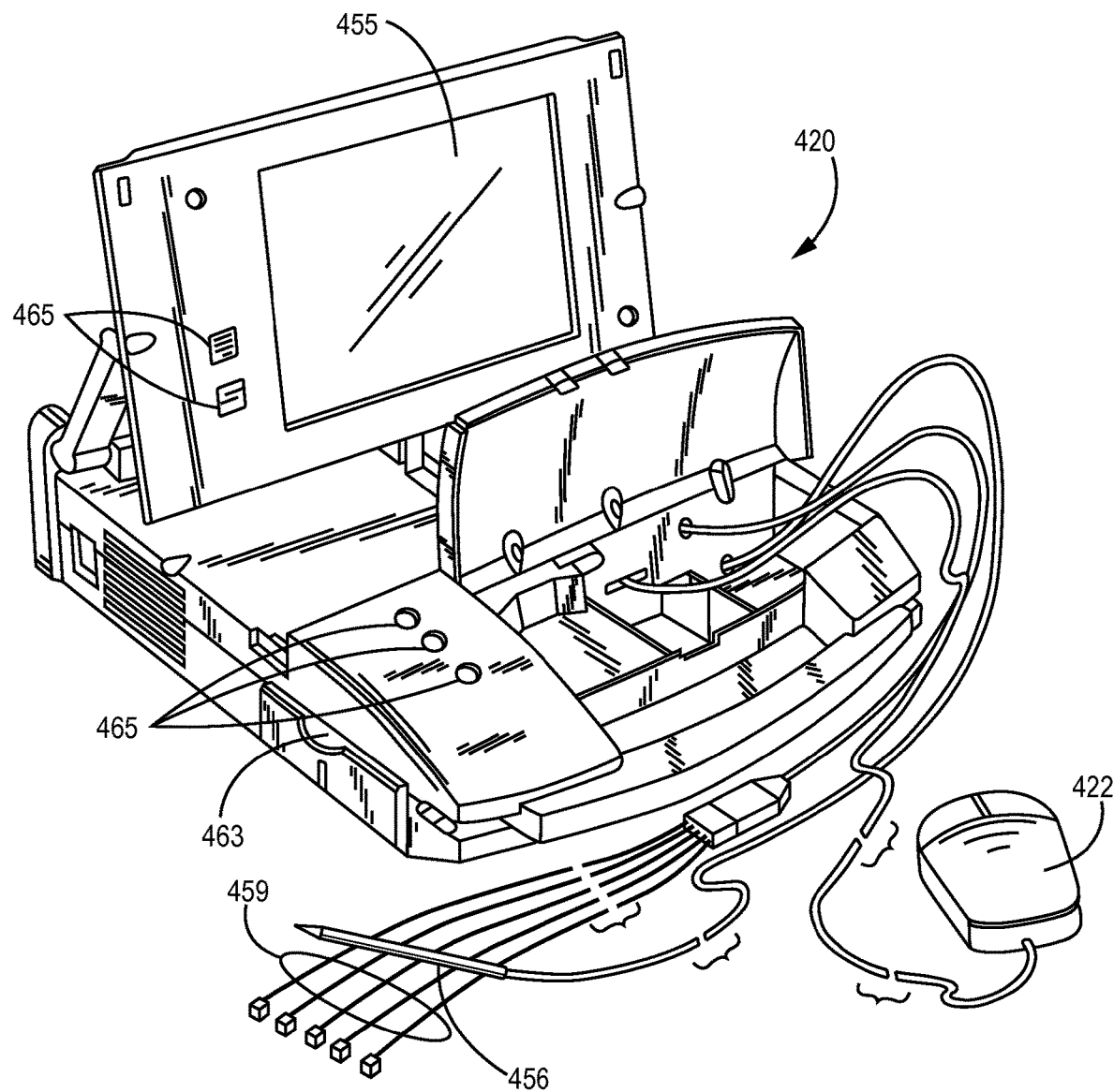
FIG. 4 is a perspective view of a programmer of a type useful in practicing the present disclosure.

FIG. 4 is a plan view of an external programmer of a sort appropriate for use in conjunction with the practice of the present disclosure in conjunction with any of the devices of FIGS. 1-3. The programmer 420 is a microprocessor controlled device which is provided with a programming head 422 for communicating with an implanted device, a set of surface electrogram electrodes 459 for monitoring a patient's electrogram, a display 455 which is preferably a touch sensitive display, control buttons or keys 465, and a stylist 456 for use in conjunction with the touch sensitive screen 455. By means of the control keys 465 and the touch sensitive screen 455 and stylus 456, the physician may format commands for transmission to the implantable device. By means of the screen 455, the physician may observe information telemetered from the implantable device. The programmer is further provided with a printer 463 which allows for hard copy records of displays of signals received from the implanted device such as electrograms, stored parameters, programmed parameters and information as to heart rate variability trends according to the present disclosure. While not visible in this view, the device may also be provided with a floppy disk or CD ROM drive and/or a port for insertion of expansion cards such as P-ROM cartridges, to allow for software upgrades and modifications to the programmer 420.

In the context of the present disclosure, programmer 420 may serve simply as a display device, displaying information with regard to heart rate variability as calculated by the implanted device or instead may receive uplinked raw data related to heart intervals and may calculate the heart rate trends and heart rate variability values according to the present disclosure. It is believed that it is preferable for the implanted device to perform the bulk of the computations necessary to practice the disclosure, and in particular that it is preferable for the implanted device to at least calculate median rate values, to reduce the storage requirements within the implanted device. However, allocation of functions between the implanted device and the programmer may differ from the preferred embodiments and still result in a workable system.

Figure 5:
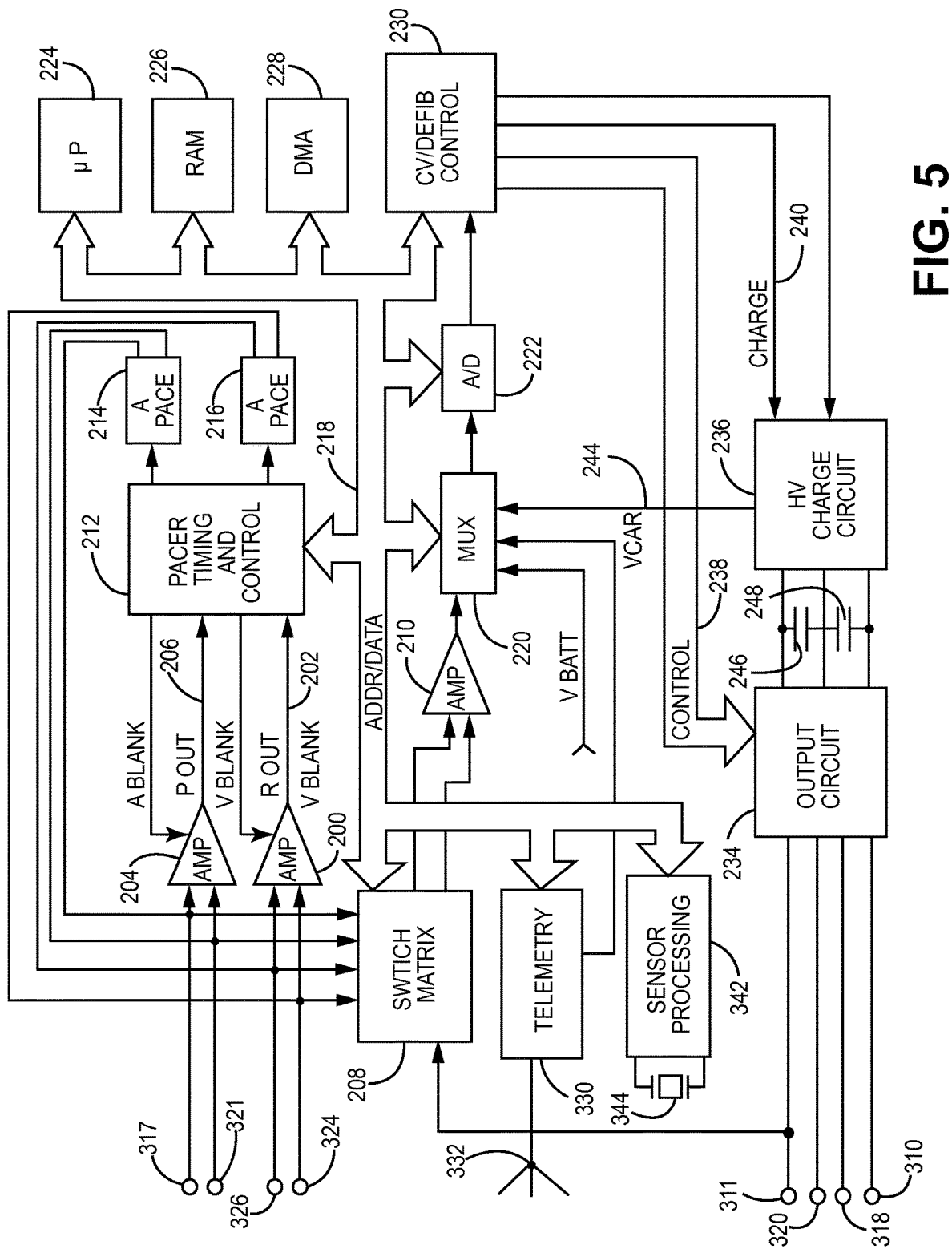
FIG. 5 is a functional schematic diagram of an implantable pacemaker/cardioverter/defibrillator of a type useful in practicing the present disclosure.

FIG. 5 is a functional schematic diagram of an implantable pacemaker/cardioverter/defibrillator of the type illustrated in FIG. 3, in which the present disclosure may usefully be practiced. This diagram should be taken as exemplary of one type of anti-tachyarrhythmia device in which the disclosure may be embodied, and not as limiting, as it is believed that the disclosure may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 1, and is the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present disclosure.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by ND converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, which patent is hereby incorporated by reference herein in its entirety. The particular telemetry system employed is not critical to practicing the disclosure, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present disclosure. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 5 may additionally is provided with an activity sensor 344, mounted to the interior surface of the device housing or to the hybrid circuit within the device housing. The sensor 344 and sensor present in circuitry 342 may be employed in the conventional fashion described in U.S. Pat. No. 4,428,378 issued to Anderson et al, incorporated herein by reference in its entirety, to regulate the underlying pacing rate of the device in rate responsive pacing modes.

The remainder of the circuitry is dedicated to the provision of cardiac pacing, cardioversion and defibrillation therapies, and, for purposes of the present disclosure may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and are used in conjunction with the present disclosure to measure heart rate variability and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 (FIG. 2) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present disclosure may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various arrhythmia detection methodologies known to the art might also usefully be employed in alternative embodiments of the disclosure.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 6:
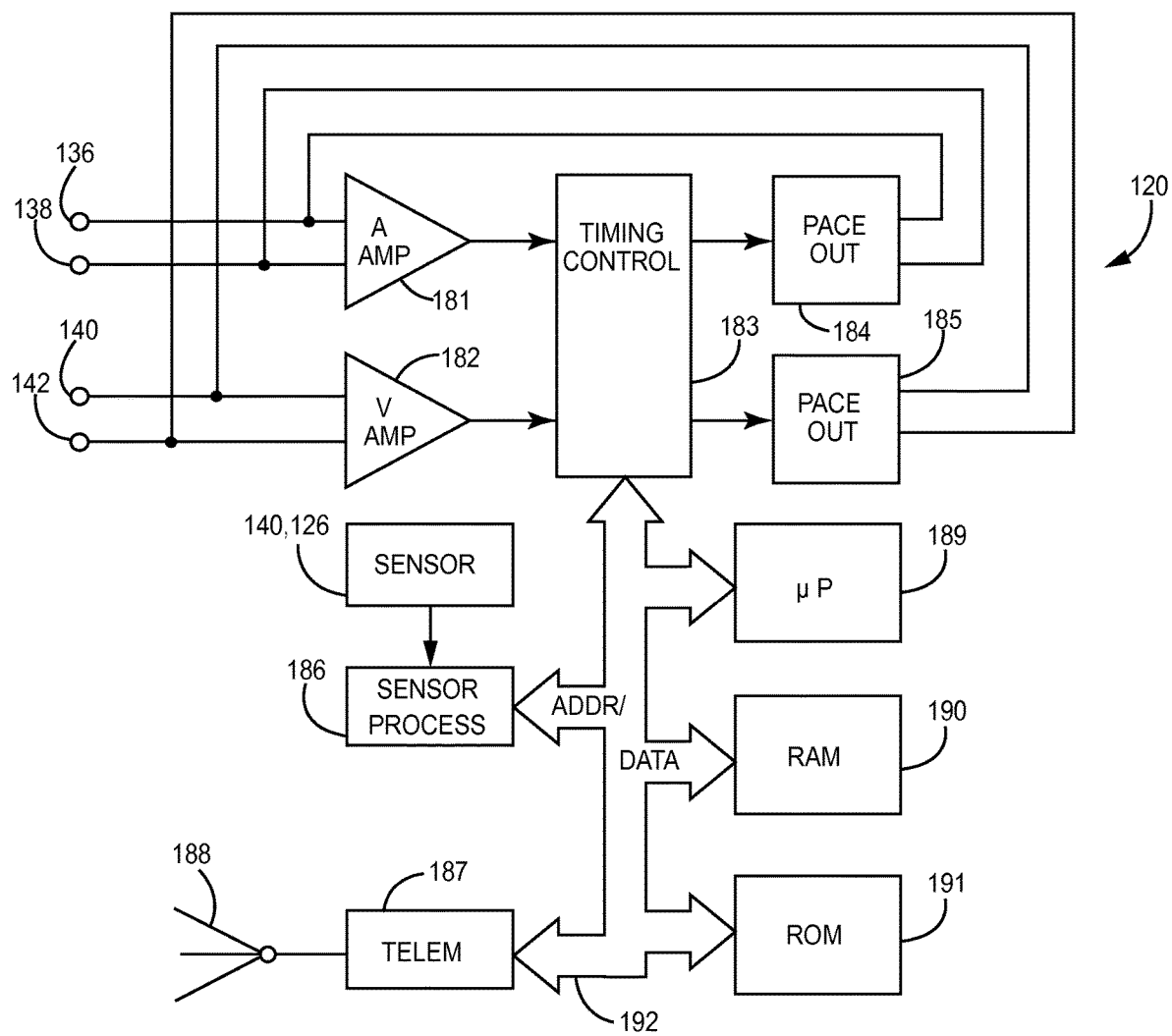
FIG. 6 is a functional schematic diagram of an implantable pacemaker of a type useful in practicing the present disclosure.

FIG. 6 is a functional schematic diagram of the pacemaker 120 illustrated in FIG. 2. The pacemaker of FIGS. 2 and 6 is essentially a set of subcomponents of the implantable pacemaker/cardioverter/defibrillator illustrated in FIGS. 1 and 5. Like the device of FIG. 5, the pacemaker is a microprocessor controlled device with microprocessor 189 operating under control of programming stored in Read Only Memory (ROM) 191. In the device as illustrated, electrodes 136 and 138, intended for location in the atrium of the patient's heart are coupled to an atrial amplifier 181 which may correspond to atrial amplifier 204 in FIG. 5. Similarly, ventricular electrodes 140 and 142 are coupled to ventricular amplifier 182, which may correspond to ventricular amplifier 200 in FIG. 5. The outputs of atrial and ventricular amplifiers 181 and 182 are input into timing and control circuitry 183 which conforms generally to the pacer timing and control circuitry 212 of FIG. 5, and which measures intervals between detected depolarizations and controls intervals between delivered pacing pulses as well as generating interrupts via data/address 192 to awake microprocessor 189 in response to delivery of a pacing pulse or sensing of a cardiac depolarization. Intervals between depolarizations measured by timing control circuitry 183 are stored in Random Access Memory (RAM) 190 until processed by microprocessor 189 to derive average heart rate values. Atrial and ventricular pacing pulses delivered according to one or more of the standard pacing modes described in conjunction with FIG. 5 are produced by atrial and ventricular pulse generator circuits 184 and 185 which may correspond to pulse generator circuits 215 and 216 in FIG. 5.

The sensor illustrated in FIG. 6 may correspond to either an activity sensor 126 as described in conjunction with FIG. 2 above or to a hemodynamic sensor 140, as described in conjunction with FIG. 2. If the sensor is an activity sensor, then sensor processing circuitry 186 may correspond to sensor processing circuitry 342 discussed in conjunction with FIG. 5. However, if the sensor is a hemodynamic sensor, the sensor processing circuitry would correspond to the sort of processing circuitry typically associated with hemodynamic sensors. Telemetry circuitry 187 in conjunction with antenna 188 serves to transmit information to and receive information from an external programmer precisely as described above in conjunction with the device of FIG. 5, including information related to stored median interval values and heart rate variability measurements in RAM 190, as calculated by microprocessor 189.

Figure 7:
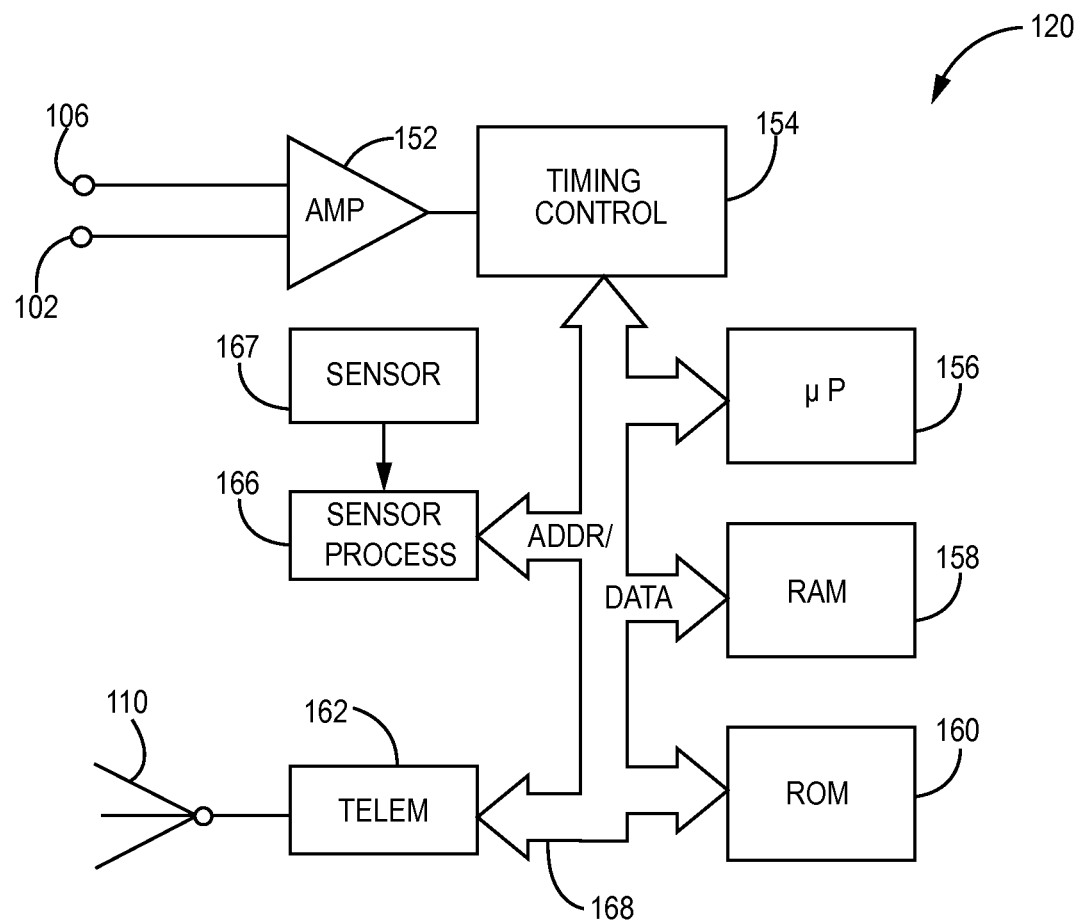
FIG. 7 is a functional schematic diagram of an implantable monitor of a type useful in practicing the present disclosure.

FIG. 7 illustrates the functional organization of the subcutaneously implantable heart monitor 100 illustrated in FIG. 3. This device consists essentially of a set of subcomponents of the more complex embodiment of the disclosure disclosed in FIG. 5, and includes a sense amplifier 152 coupled to electrodes 102 and 106, illustrated in FIG. 1. Sense amplifier 152 may correspond to sense amplifier 204 or 200 in FIG. 5. Like the device of FIG. 5, the implantable monitor may be a microprocessor control device operating under control microprocessor 156 with its functionality controlled primarily by software stored in the read only memory associated therein. In this context, amplifier 152 detects the occurrence of heart depolarizations, with timing/control circuitry 154 serving to measure the durations between the detected heart depolarizations and to generate interrupts awakening microprocessor 156 so that it may store, analyze and process the detected intervals. Random Access Memory (RAM) 158 serves to store measured and calculated parameters including the calculated median heart rate and/or heart rate variability values for later telemetry to an external device. Like the device in FIG. 5, timing and control circuitry communicates with the microprocessor and the remaining circuitry by means of the address/data bus 168. Telemetry system 162 may correspond to telemetry system 330 in FIG. 5 and, via antenna 110 transmits and receives information from the external programmer, including transmitting information with regard to the calculated median rate values and heart variability values stored in RAM 158. Sensor 112 may correspond to sensor 344 in FIG. 5 and it may be a physical activity sensor as discussed above. The output of sensor 112 is passed through sensor processing circuitry 166 which may correspond to sensor processing circuitry 342 in FIG. 5.

Figure 8:
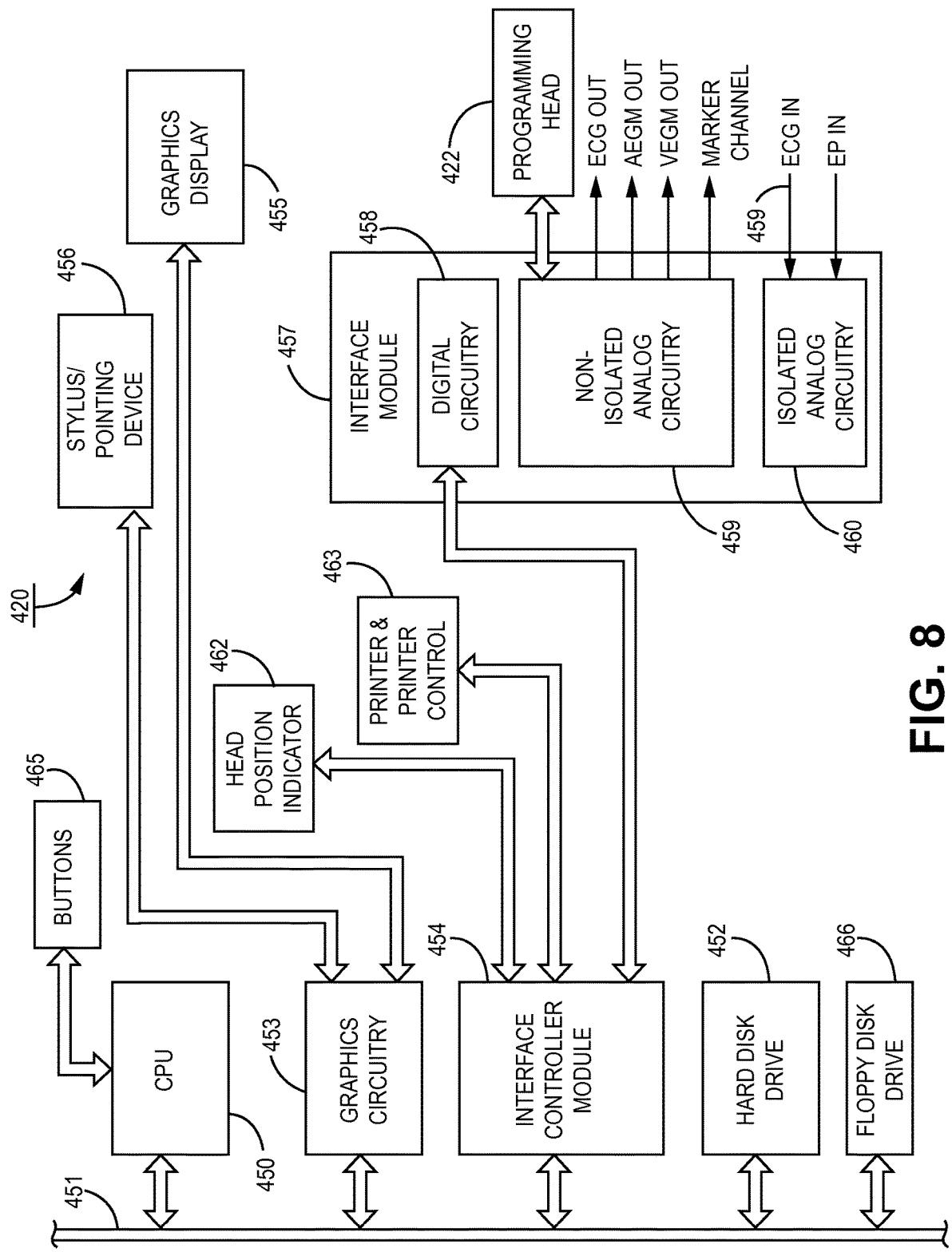
FIG. 8 is a functional schematic diagram of a programmer of a type useful in practicing the present disclosure.

FIG. 8 is a functional schematic of a programmer as illustrated in FIG. 4 appropriate for use in conjunction with the disclosure. Programmer 420 is a personal computer type, microprocessor-based device incorporating a central processing unit 450, which may be, for example, an Intel 80386 or 80486 or Pentium microprocessor or the like. A system bus 451 interconnects CPU 450 with a hard disk drive 452 storing operational programs and data and with a graphics circuit 453 and an interface controller module 454. A floppy disk drive 466 or a CD ROM drive is also coupled to bus 451 and is accessible via a disk insertion slot within the housing of the programmer 420. Programmer 420 further comprises an interface module 457 which includes digital circuit 458, non-isolated analog circuit 459, and isolated analog circuit 460. Digital circuit 448 enables interface module 457 to communicate with interface controller module 454.

In order for the physician or other care giver or user to communicate with the programmer 420, control buttons 465 or optionally a keyboard coupled to CPU 50 are provided. However the primary communication mode is through graphics display screen 455 of the well-known "touch sensitive" type controlled by graphics circuit 453. A user of programmer 420 may interact therewith through the use of a stylus 456, also coupled to graphics circuit 453, which is used to point to various locations on screen 455 which display menu choices for selection by the user or an alphanumeric keyboard for entering text or numbers and other symbols.

Graphics display 455 also displays a variety of screens of telemetered out data or real time data including measurements of heart rate variability and heart rate trends according to the present disclosure. Programmer 420 is also provided with a strip chart printer 463 or the like coupled to interface controller module 454 so that a hard copy of a patient's ECG, EGM, marker channel or of graphics displayed on the display 455 can be generated.

As will be appreciated by those of ordinary skill in the art, it is often desirable to provide a means for programmer 20 to adapt its mode of operation depending upon the type or generation of implanted medical device to be programmed. Accordingly, it may be desirable to have an expansion cartridge containing EPROMs or the like for storing software programs to control programmer 420 to operate in a particular manner corresponding to a given type or generation of implantable medical device. In addition, in accordance with the present disclosure, it is desirable to provide the capability through the expansion cartridge or through the floppy disk drive 66 or CD ROM drive.

The non-isolated analog circuit 459 of interface module 457 is coupled to a programming head 422 which is used to establish the uplink and downlink telemetry links between the pacemaker 410 and programmer 420 as described above.

Uplink telemetered EGM signals are received in programming head 422 and provided to non-isolated analog circuit 459. Non-isolated analog circuit 459, in turn, converts the digitized EGM signals to analog EGM signals and presents these signals on output lines A EGM OUT and V EGM OUT. These output lines may then be applied to a strip-chart recorder 463 to provide a hard-copy printout of the A EGM or V EGM for viewing by the physician. Similarly, the markers be received by programming head 422 are presented on the MARKER CHANNEL output line from non-isolated analog circuit 459.

Isolated analog circuit 460 in interface module 547 is provided to receive external ECG and electrophysiologic (EP) stimulation pulse signals. In particular, analog circuit 460 receives ECG signals from patient skin electrodes 459 and processes these signals before providing them to the remainder of the programmer system in a manner well known in the art. Circuit 460 further operates to receive the EP stimulation pulses from an external EP stimulator for the purposes of non-invasive EP studies, as is also known in the art.

In order to ensure proper positioning of programming head 422 over the antenna of the associated implanted device, feedback is provided to the physician that the programming head 422 is in satisfactory communication with and is receiving sufficiently strong RF signals. This feedback may be provided, for example, by means of a head position indicator, e.g. a light-emitting diode (LED) or the like that is lighted to indicate a stable telemetry channel.

Figure 9:
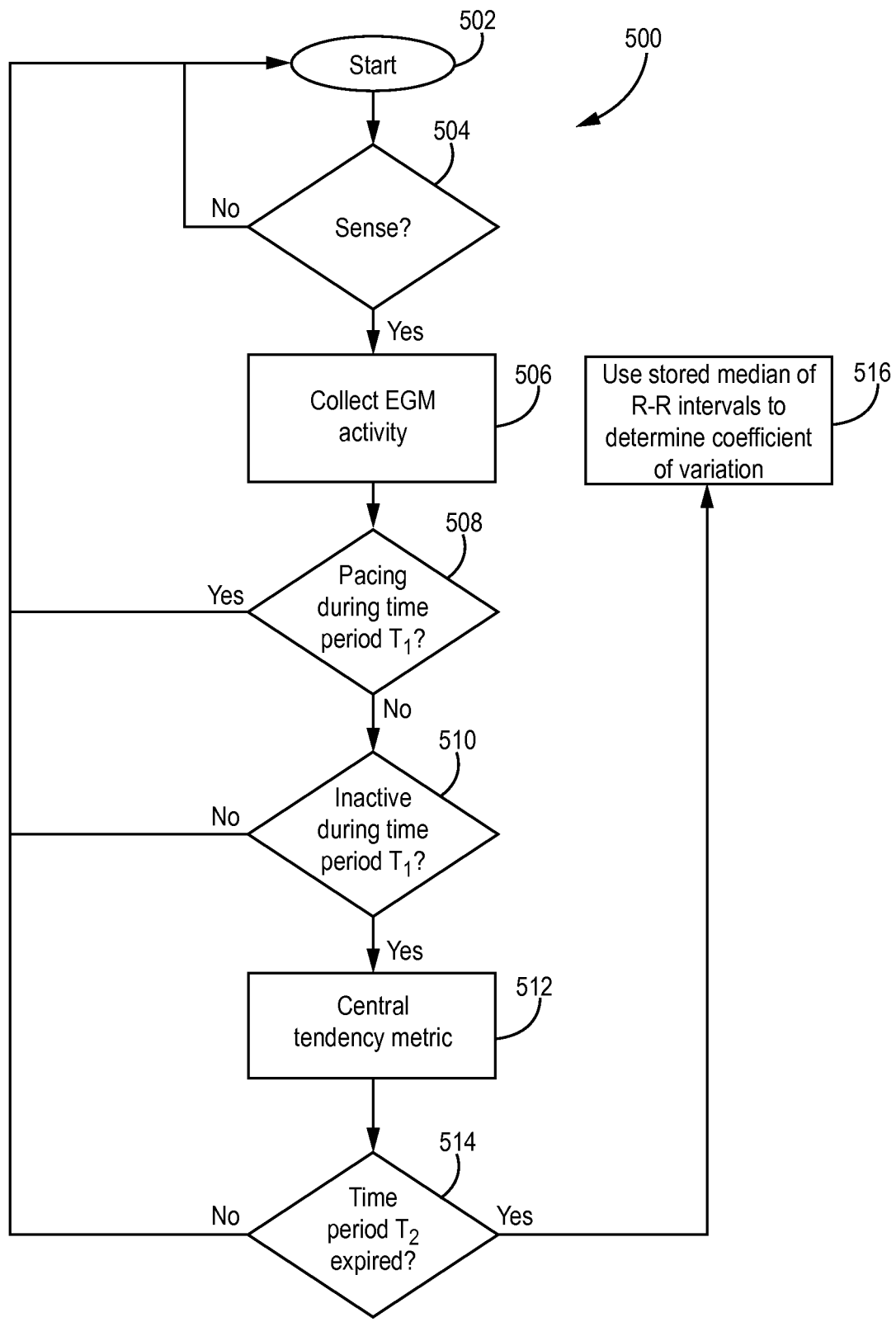
FIG. 9 is a functional flow chart illustrating a method of monitoring heart rate variability which may be employed in conjunction with the present disclosure.

FIG. 9 is a functional flow chart illustrating the overall method of operation 500 of a device according to the present disclosure in monitoring heart intervals and in calculating a standard deviation of heart rate variability for display on external programmer. In one or more embodiments, heart interval, as applied herein, is exemplified as a sensed atrial depolarization (first sensed depolarization) extending to a next sensed atrial depolarization (second sensed depolarization) in the same atria. The sensed atrial depolarization extending to a next sensed heart depolarization in the same atria is referred to as A-A measurements. In one or more other embodiments, heart interval is exemplified as a sensed ventricular depolarization (first sensed depolarization) extending to a next sensed ventricular depolarization (second sensed depolarization) in the same ventricle. The sensed ventricular depolarization extending to a next sensed ventricular depolarization in the same ventricle is referred to as V-V measurements. A-A measurements are preferred since A-A measurements remove the confounding effect of AV node delays.

In conjunction with the flow chart of FIG. 9, it should be understood that the operations illustrated are all presumed to take place in the implanted device, which is a preferred embodiment of the disclosure. In this context, all calculations and processing of the measured heart intervals can be performed by the microprocessor within the implanted device. However, in alternative embodiments, one or more steps of the method for determining heart rate variability may be performed in the external device, based on information telemetered to the external device by the implanted device. Additionally, it should be understood that regardless as to whether the present disclosure is employed by an implantable medical device or an external device, each time a calculation is performed or data is measured, the result is automatically stored by computer instructions (e.g. firmware etc.) and/or can be stored as part of the present disclosure.

Method 500 starts at block 502 in which variables are set to zero. For example, time period (T1), described in greater detail below, is set to zero for every monitoring period T2 (e.g. 24 hour time period). At block 504, the microprocessor determines whether an electrical signal such as an atrial depolarization is sensed from cardiac tissue by an electrode 17 and 21 associated with the atrial/SVC lead 15. Measurements can also be made using sensed ventricular events (i.e. not just atrial events).

Figure 13:
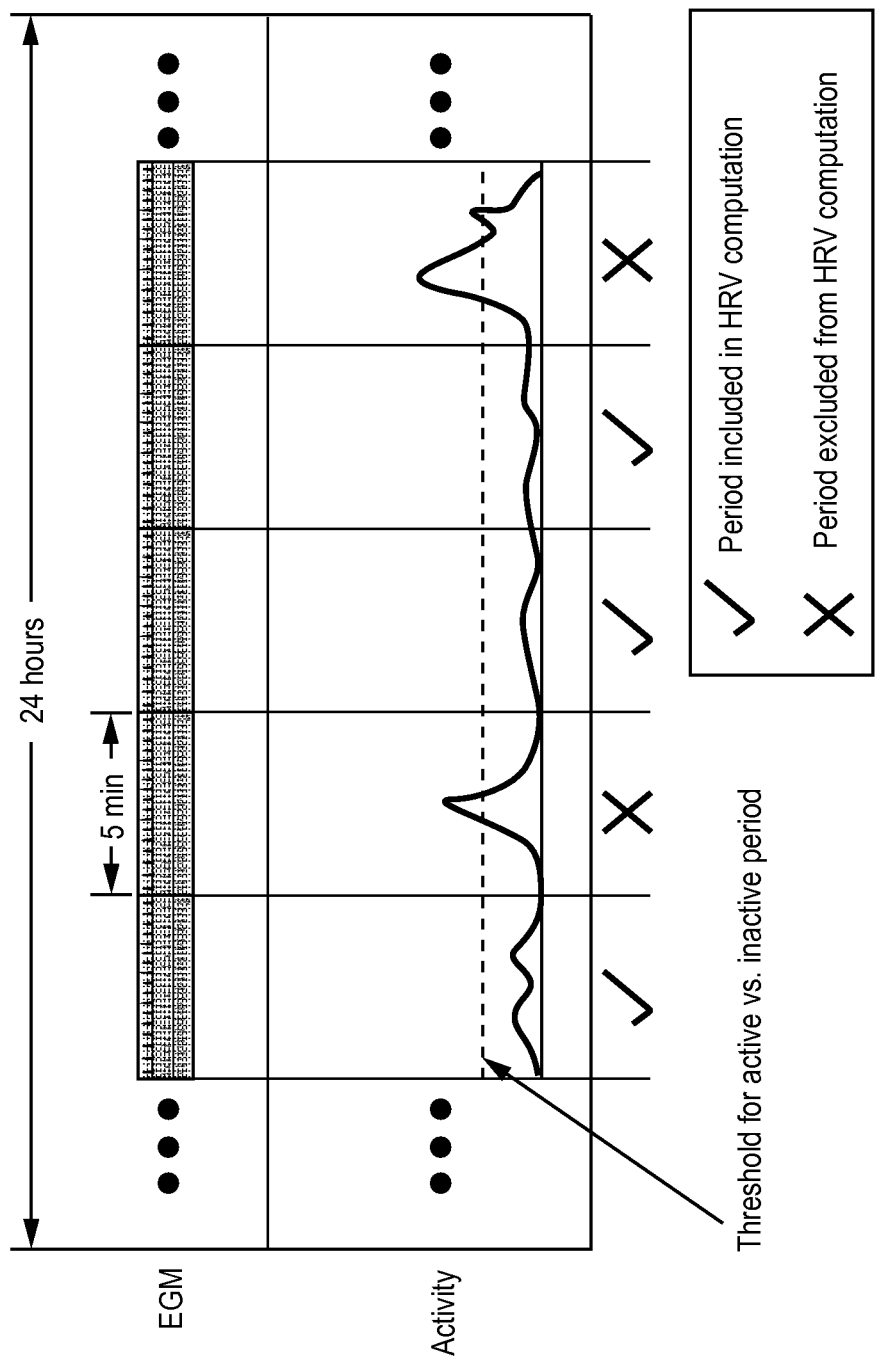
FIG. 13 is an exemplary view of an EGM and corresponding activity levels depicting time periods that are included in the heart rate variability computation.

The NO path from block 504 causes the device to determine whether EGM activity should be rejected or not collected. FIGS. 13-14 provide examples of an EGM with corresponding activity levels depicted over time periods that are included (represented by the "√") in the heart rate variability computation while other time periods (represented by the "X") are excluded. The time periods that are excluded exceed an activity threshold level, which can be set by the user at the time of implant or during a checkup at a physician's office.

FIG. 14 is an exemplary view of active (represented by "A") and inactive (represented by "I") interval data summarized over T2 (i.e. a twenty four (24) hour period of time). Active periods are shown as being deleted (i.e. struck out) since active periods are automatically eliminated from the heart rate variability calculation. The heart rate variability calculation includes all of the listed inactive periods (i.e. rest periods) within the T2.

In addition to the criteria of excluding active periods, certain other intervals are excluded as a function of the type of device employed to monitor heart rate variability and/or the status of the patient in whom the device is implanted. For example, in the case of a patient who is subject to atrial or ventricle tachycardia in which the device employing the present disclosure is an implantable pacemaker or pacemaker/cardioverter/defibrillator, it is desirable to discard all intervals beginning with a paced depolarization. It may also be desirable to discard all heart intervals associated with detection and treatment of tachyarrhythmias. For example all heart intervals which meet tachyarrhythmia detection criteria due to their relatively short duration, all heart intervals obtained during charging of the output capacitors of such a device prior to delivery of a cardioversion or defibrillation shock and all intervals sensed during delivery of anti-tachyarrhythmia therapies such as anti-tachycardia pacing, cardioversion and defibrillation may be discarded. In addition to or as an alternative, in cases in which the disclosure is embodied in the context of a dual chamber pacemaker capable of switching between various pacing modes in response to detected atrial tachyarrhythmias, it may be desirable to discard heart intervals measured during operation of the mode switch between pacing modes. In contrast, if the patient has a simple VVI type pacemaker, and is not subject to tachyarrhythmias, there may be no need to discard any collected heart intervals except those beginning in paced depolarizations. Even if some or all of these heart intervals are to be discarded, selection of intervals to be discarded does not require the ability to distinguish between normally conducted and ectopic beats, but only the ability to either measure the durations between depolarizations and/or the underlying operative states of the device.

An atrial depolarization of the patient's heart sensed via a P wave amplifier electrically coupled to atrial electrodes at block 504 causes the YES path to continue to block 506 in which all EGM activity is stored into memory for a short pre-specified time period designated as T1 at block 506. In an alternative embodiment, a ventricular depolarization of the patient's heart sensed via a R wave amplifier electrically coupled to ventricular electrodes at block 504 causes the YES path to continue to block 506 in which all EGM activity is stored into memory for a short pre-specified time period designated as T1 at block 506. T1 may be, for example, time periods of one to 20 minutes, preferably about 5 minutes. At the end of T1, the device optionally stops collecting EGM activity in order to preserve power of the device.

At block 508, a determination is made as to whether pacing has occurred during the pre-specified time period T1. If pacing has occurred, the YES path from block 508 returns to block 502 in which method 500 can be again performed. If pacing has not occurred, the NO path from block 508 continues to block 510 in which a determination is made as to whether the patient has been inactive during the pre-specified time period T1. The present disclosure employs an activity sensor 30 to determine when the patient is at rest or is inactive. After storing the presence (or absence) of activity into memory, the median of R-R intervals is determined. An example of the median of R-R intervals is presented in FIG. 14. The median of R-R intervals is taken of all the R-R intervals collected over a 5 minute period.

Figure 10:
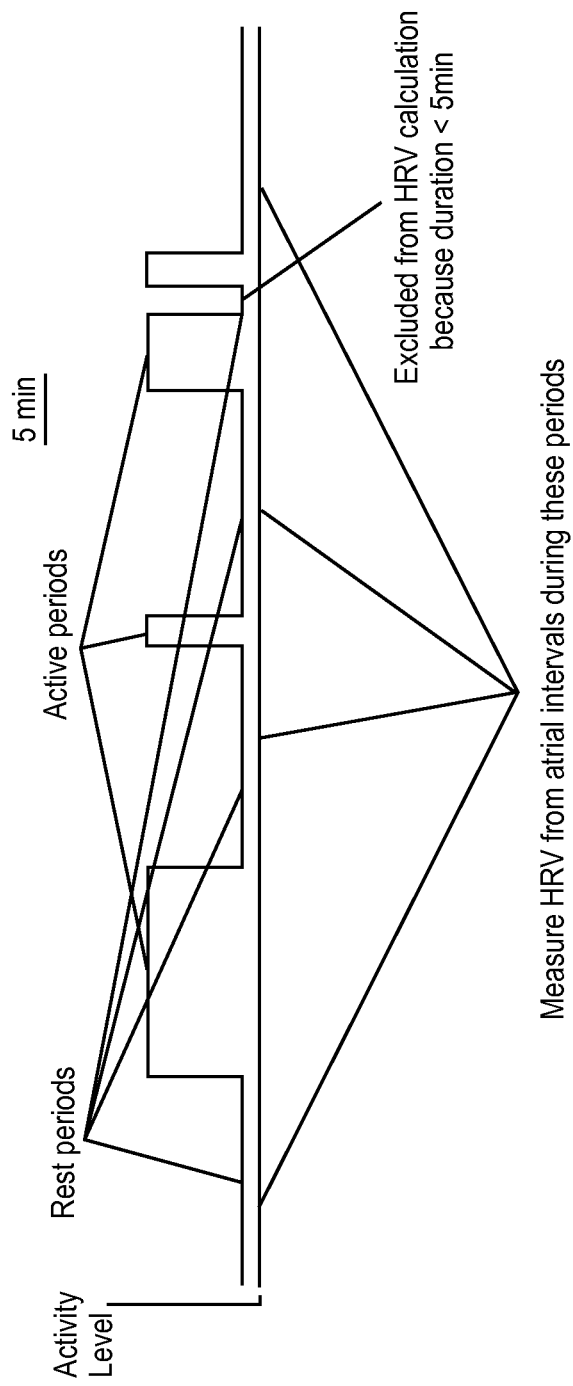
FIG. 10 is a schematic diagram of heart rate variability measurements relative to a patient's activity level, active periods, and rest periods.

FIG. 10 depicts exemplary rest periods and active periods that extend different lengths of time over a monitoring period T2 (e.g. 24 hour time period). Active periods are distinguished rest periods by microprocessor acquiring signals from activity sensor 30. In one or more embodiments, heart rate variability measurements solely employ rest periods that extend at least a predetermined amount of time T1 such as five minutes or longer continuous periods of rest. If the rest period is longer than T1, then the rest period is parsed or segmented into T1 (i.e. 5-minute) atrial intervals. The duration of the atrial interval can be set by the user. Typically, the interval is less than 10 minutes and is preferably set at 5 minutes.

Rest periods that do not extend the same amount of time as T1 are automatically rejected from use in determining the heart rate variability. Additionally, all active periods are automatically rejected. Median atrial intervals are computed for various rest intervals that extend at least T1. In one or more other embodiments, a central tendency interval is used for a pre-specified period of time T1 (e.g. 5 minute periods). Central tendency metrics includes arithmetic mean, median, and mode. For purposes of illustration, median will be used as an example of central tendency metrics. At block 512, the median of the A-A intervals or R-R intervals is determined over the pre-specified time period. For example, the set of R-R intervals, tracked during the pre-specified time period (i.e. 5 minutes), can be determined by arranging all the observations from lowest value to highest value and picking the middle one (e.g., the median of {3, 5, 9} is 5). Assume over a 5 minute interval, 300 intervals occur (i.e. 1 interval is typically 1 second (60 bpm) therefore 5×60=300). The number of R-R intervals are tracked by the processor. The selected median is then stored into memory for that time period, as shown in FIG. 14.

At block 514, a determination is made as to whether a predetermined amount of time has expired T2. The predetermined amount of time reflects the entire time in which sum of all calculated median values of heart intervals separating depolarizations of the chamber of the heart, e.g. atrial or ventricular depolarizations. In one or more embodiments, the predetermined amount of time is a 24 hour period.

If the longer time period T2 has not expired at 514, the device returns to restart timing of the next shorter period T1 at 502 and continues to collect heart rate intervals and calculate interval medians until expiration of the longer time period T2. Following the expiration of the longer time period T2 at 514, the device proceeds to calculate the coefficient of variation (CV) using the stored median of R-R intervals at block 516. The CV is defined as the ratio of the standard deviation σ to the mean μ:

$$c_v = \frac{\sigma}{\mu}$$

CV shows the extent of variability in relation to mean of the population. Standard deviation, an example of CV, is solely used to illustrate the techniques described herein. Standard deviation equations of all normal-to-normal (SDNN) or standard deviation of average normal-to-normal (SDANN) indices, described in U.S. Pat. No. 5,749,900 issued to Schroeppel et al. and U.S. Pat. No. 5,411,031 issued to Yomtov, and U.S. Pat. No. 6,508,771 are all incorporated by reference in their entirety.

The standard deviation of the median R-R intervals produces the heart rate variability, which is then stored in the implanted device for later telemetry to an external device. As noted above, it is believed that in some cases the allocation of functions between the external and internal device employed to practice the disclosure may be somewhat different. For example, instead of actually calculating the value of median and/or standard deviation according to the present disclosure, the implanted device may simply store the values of median and/or standard deviation, so that the external device may later perform the calculation of median and/or standard deviation according to the present disclosure. It is also possible that in some embodiments, the device may simply collect the values of undiscarded heart intervals, for later uplinking to external device wherein the calculation of median values and the heart rate variability median and/or standard deviation may thereafter be undertaken. However, this embodiment is believed less desirable in that it requires substantial additional data storage base within the implanted device. In another embodiment, the IMD 10 simply stores A-A intervals along with a patient's corresponding activity status sensed from activity sensor 30. The stored data is then wirelessly transmitted to an external network system. An exemplary external network system is the Medtronic CareLink® network that can be used to receive data from patients and then automatically perform calculations and optionally generate diagnostic reports to physicians. In this embodiment, the external network system computes HRV using the logic shown and described relative to FIGS. 9-10 i.e. implantable device does not perform any computation on its own. Instead, the IMD merely collects the relevant data and transmits the data to the external network system.

The median atrial interval is determined from all rest period durations over the extended period of time T2 (e.g. 24-hour period etc.) that are used to compute true heart rate variability at rest by calculating the standard deviation of all median intervals. Thereafter, standard deviation of the median atrial intervals is computed to determine HRV.

Figure 11:
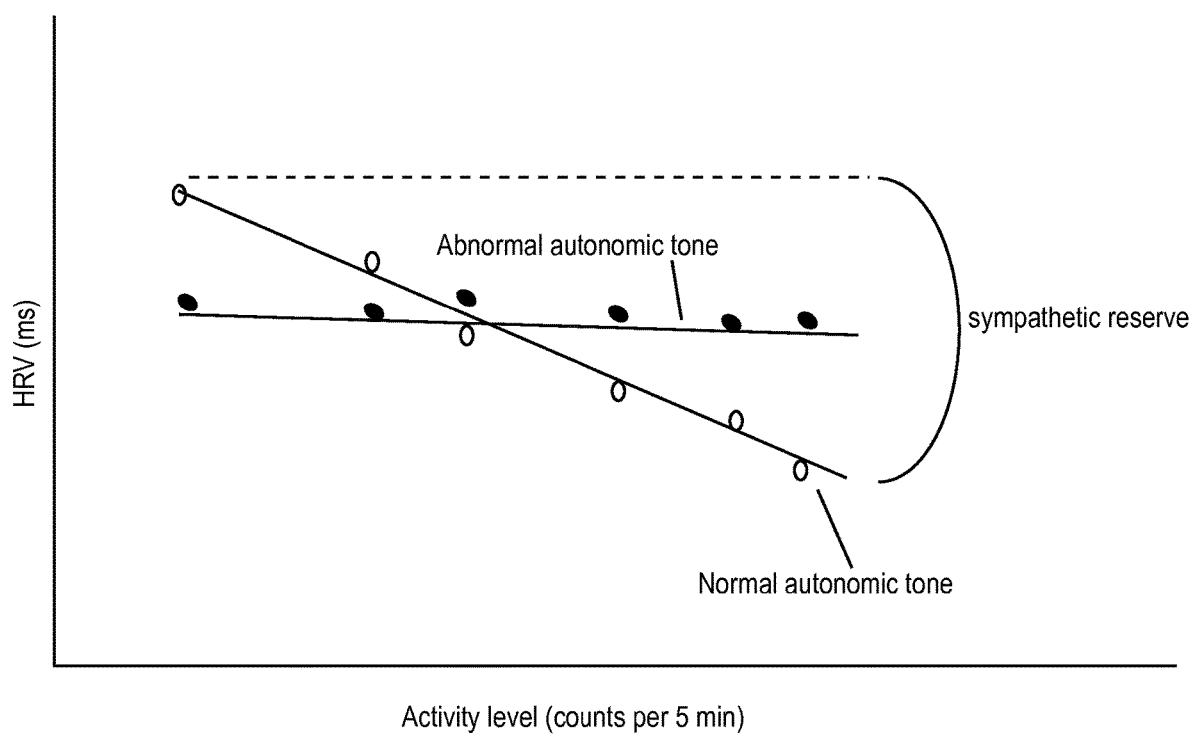
FIG. 11 is a schematic diagram of heart rate variability measurement as a function of activity level to estimate slope and sympathetic reserve.
Figure 12:
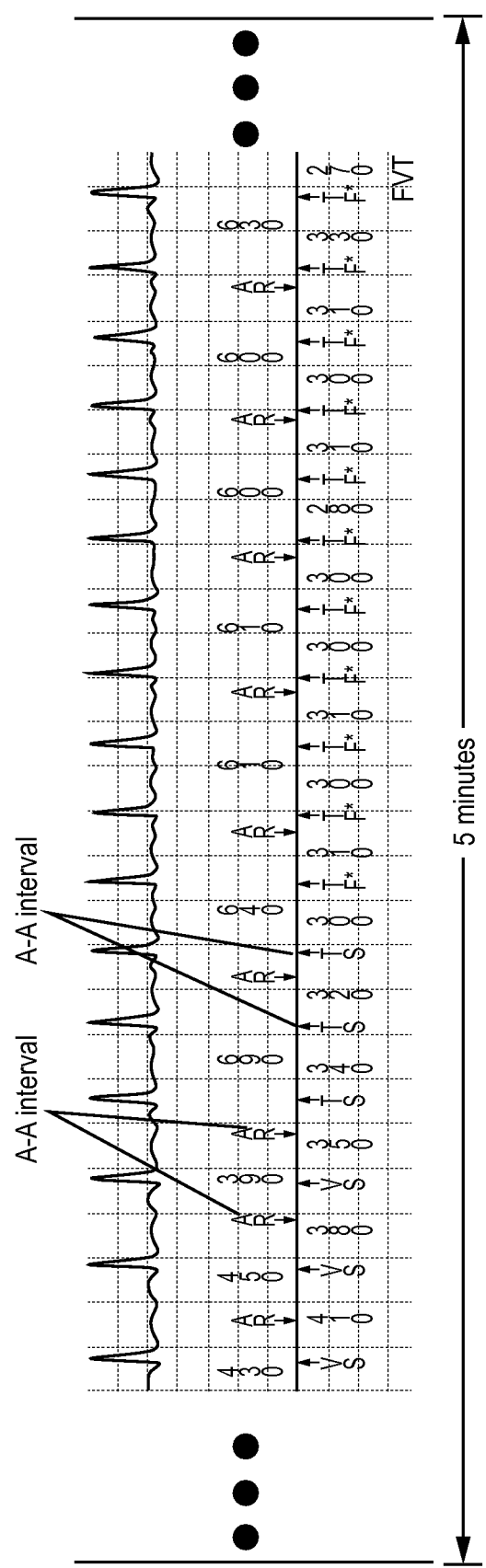
FIG. 12 is an exemplary electrocardiogram (EGM) showing atria to atria (A-A) intervals over a five minute period.

Once the true basal HRV at rest is known, sympathetic reserve can be determined by measuring HRV during various levels of activity. A measure of intensity of activity can be obtained by noting the activity counts over the corresponding T1 duration during which median atrial rate is computed. The HRV can then be plotted against the activity level to get sympathetic reserve. A larger negative slope is an indicator of normal autonomic tone, and depressed HRV at rest along with a decrease in slope is an indicator of abnormal autonomic tone (FIG. 11). Such diagnostics information can help clinicians with better management of patients (e.g. titrating a drug dose) and identifying high risk patients (e.g. patients at risk of heart failure events). An example of modifying therapy may involve a low HRV (i.e. sympathetic tone is high), which could automatically cause the adjustment of electrical stimulation delivered by a neurostimulator to nerve tissue (e.g. vagal nerve), FIG. 11 depicts HRV and activity level as determined through activity counts over five minute time periods. HRV is plotted as function of activity level (using counts per 5-minutes as a surrogate) to estimate slope and sympathetic reserve. HRV depressed at the baseline (i.e. at rest) and a shallow slope is an indicator of autonomic imbalance. The simplified heart rate variability method presented herein consumes less energy and provides more accurate and useful data than conventional devices. Specifically, by using an activity sensor to detect periods of rest and computing the true basal heart rate variability solely upon the rest periods, a more accurate heart rate variability measurement is made. Additionally, heart rate variability at varying activity level can be used to estimate robustness of an estimated sympathetic tone (i.e. sympathetic reserve). Moreover, any abnormality in autonomic tone can be estimated through the method described herein.

In contrast, conventional heart rate variability computations do not calculate basal heart rate variability. Conventional heart rate variability measures median atrial interval value every five minutes and then computes the standard deviation of these intervals over a 24 hour period. Conventional methods may show the heart rate variability decreases during a period of activity. Accordingly, the heart rate variability reported by a conventional device is not a true measure of basal autonomic tone at rest.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A cardiac pacemaker system for monitoring a patient's heart rate variability comprising:
   means for delivering a cardiac pacing therapy including delivery of cardiac pacing pulses to trigger paced depolarizations;
   a sensing electrode to detect cardiac depolarizations;
   a sense amplifier coupled to the sensing electrode to produce signals indicative of detected cardiac depolarizations;
   an activity sensor to generate a signal indicative of activity;
   means for measuring intervals between successive cardiac depolarizations, including intervals initiated by said paced depolarizations;
   a timing means for defining successive shorter time periods during a longer monitoring period;
   means for using the signal for determining whether the patient is active;
   means for using data from the signal for determining rest periods that extend as long as the shorter time period;
   means for determining cardiac intervals occurring during each rest period;
   storing means for storing the measured cardiac intervals; and
   means for calculating a central tendency metric of the measured cardiac intervals during each rest period and in response to calculating the central tendency metric, determining a coefficient of variation of the cardiac intervals during the rest periods within the longer monitoring period to generate the heart rate variability; and
   means for employing the heart rate variability to modify the therapy delivered by the means for delivering a cardiac pacing therapy.

2. The cardiac pacemaker system of claim 1 wherein the cardiac pacemaker system comprises an implantable medical device.

3. A cardiac pacemaker system according to claim 1 wherein the device is external to a patient.

4. A cardiac pacemaker system according to claim 1, further comprising means for rejecting measured cardiac depolarization intervals that begin with a paced depolarization.

5. A cardiac pacemaker system according to claim 1, further comprising means for rejecting measured cardiac depolarization intervals occurring during tachyarrhythmias and wherein the calculating means comprises means for calculating median measured cardiac depolarization intervals based only on measured cardiac depolarization intervals not rejected.

6. A cardiac pacemaker system according to claim 5 further comprising means for determining a total duration of the non-rejected measured cardiac depolarization intervals occurring during the shorter time periods, and means for preventing calculation of a median measured cardiac depolarization interval for the preceding shorter time period if the total duration of non-rejected measured cardiac depolarization intervals during a shorter time period is less than a required duration.

7. A cardiac pacemaker system according to claim 6, further comprising:

means for rejecting measured cardiac depolarization intervals occurring during tachyarrhythmias and wherein the calculating step comprises calculating median measured cardiac depolarization intervals based only on measured cardiac depolarization intervals not rejected.

8. A cardiac pacemaker system according to claim 7 wherein the calculating step comprises determining a total duration of the non-rejected measured cardiac depolarization intervals during the shorter time periods and preventing calculation of a median measured cardiac depolarization interval if the total duration of non-rejected heart intervals during a shorter time period is less than a required duration.

9. A cardiac pacemaker system according to claim 1 wherein the cardiac interval is a sensed atrial depolarization extending to a next sensed atrial depolarization in a same atria.

10. A cardiac pacemaker system according to claim 1 wherein the cardiac interval is a sensed ventricular depolarization extending to a next sensed ventricular depolarization in a same ventricle.

11. A cardiac pacemaker system according to claim 1 wherein the cardiac interval is 10 minutes or less.

12. A cardiac pacemaker system according to claim 1 wherein the cardiac interval is a user programmable interval.

13. A cardiac pacemaker system according to claim 1 wherein the coefficient of variation includes standard deviation.

14. A cardiac pacemaker system according to claim 1 wherein the delivered therapy comprises electrical stimulation and wherein modification of the delivered therapy comprises modification of the electrical stimulation.

15. A pacemaker system for monitoring a patient's heart rate variability comprising:

means for delivering a cardiac pacing therapy including delivery of cardiac pacing pulses to trigger paced depolarizations;

a sensing electrode to detect cardiac depolarizations;

a sense amplifier coupled to the sensing electrode to produce signals indicative of detected cardiac depolarizations;

an activity sensor to generate a signal indicative of activity;

means for measuring intervals between successive cardiac depolarizations;

a timing means for defining successive shorter time periods during a longer monitoring period;

means for using the signal for determining whether the patient is active;

means for using data from the signal for determining rest periods that extend as long as the shorter time period;

means for determining cardiac intervals occurring during each rest period;

storing means for storing the measured cardiac intervals; and means for calculating a central tendency metric of the measured cardiac intervals during each rest period and in response to calculating the central tendency metric, determining a coefficient of variation of the cardiac intervals during the rest periods within the longer monitoring period to generate the heart rate variability; and means for employing the heart rate variability to modify the therapy delivered by the means for delivering a cardiac pacing therapy.

16. A cardiac pacemaker system according to claim 15 wherein the device is an implantable medical device.

17. A cardiac pacemaker system according to claim 15, further comprising means for rejecting measured cardiac depolarization intervals that begin with a paced depolarization.

18. A cardiac pacemaker system according to claim 15, further comprising means for rejecting measured cardiac depolarization intervals occurring during tachyarrhythmias and wherein the calculating means comprises means for calculating median measured cardiac depolarization intervals based only on measured cardiac depolarization intervals not rejected.

19. A cardiac pacemaker system according to claim 18 further comprising means for determining a total duration of the non-rejected measured cardiac depolarization intervals occurring during the shorter time periods, and means for preventing calculation of a median measured cardiac depolarization interval for the preceding shorter time period if the total duration of non-rejected measured cardiac depolarization intervals during a shorter time period is less than a required duration.

20. A cardiac pacemaker system according to claim 19, further comprising:

means for rejecting measured cardiac depolarization intervals occurring during tachyarrhythmias and wherein the calculating step comprises calculating median measured cardiac depolarization intervals based only on measured cardiac depolarization intervals not rejected.

21. A cardiac pacemaker system according to claim 20 wherein the calculating step comprises determining a total duration of the non-rejected measured cardiac depolarization intervals during the shorter time periods and preventing calculation of a median measured cardiac depolarization interval if the total duration of non-rejected heart intervals during a shorter time period is less than a required duration.

22. A cardiac pacemaker system according to claim 15 wherein the delivered therapy comprises electrical stimulation and wherein modification of the delivered therapy comprises modification of the electrical stimulation.

* * * * *